United States Patent [19]
Schinzer et al.

[11] Patent Number: 6,043,372
[45] Date of Patent: Mar. 28, 2000

[54] INTERMEDIATES IN THE PROCESS FOR PREPARING EPOTHILONES

[75] Inventors: Dieter Schinzer, Braunschweig, Germany; Anja Limberg, Newport Beach, Calif.; Oliver M. Böhm, Magdeburgh, Germany; Armin Bauer; Martin Cordes, both of Braunschweig, Germany

[73] Assignee: Novartis AG, Basel, Switzerland

[21] Appl. No.: 09/344,713

[22] Filed: Jun. 25, 1999

Related U.S. Application Data

[62] Division of application No. 08/921,512, Sep. 2, 1997
[60] Provisional application No. 60/027,480, Sep. 26, 1996.

[30] Foreign Application Priority Data

Aug. 30, 1996 [DE] Germany ............................ 196 36 343
Oct. 28, 1996 [DE] Germany ............................ 196 45 361
Oct. 28, 1996 [DE] Germany ............................ 196 45 362

[51] Int. Cl.$^7$ .............................. C07D 277/24; C07F 7/02
[52] U.S. Cl. ........................................... 548/110; 848/203
[58] Field of Search ...................... 548/110, 203

[56] References Cited

U.S. PATENT DOCUMENTS 5,461,169 10/1995 Nicolaou et al. ...................... 549/510

FOREIGN PATENT DOCUMENTS

| | | |
|---|---|---|
| WO 93/10121 | 5/1993 | WIPO . |
| WO 97/19086 | 5/1997 | WIPO . |
| WO 98/22461 | 5/1998 | WIPO . |
| WO 98/25929 | 6/1998 | WIPO . |
| WO 99/01124 | 1/1999 | WIPO . |
| WO 99/02514 | 1/1999 | WIPO . |
| WO 99/07692 | 2/1999 | WIPO . |

OTHER PUBLICATIONS

Grubbs, R.H. et al., Acc. Chem. Res., vol. 28, pp. 446–452 (1995).
Gerth, K. et al., J. Antibiot., vol. 49, No. 6, pp., 560–563 (1996).
Bollag, M.D. et al., Cancer Res., vol. 55, pp. 2325–2333 (1995).
Meyers, A.I. et al., J.Org.Chem., vol. 38, pp. 2136–2143 (1973).
Keller–Schierliein, W. et al., Helv.Chim.Acta., vol. 4, pp. 1253–1261 (1983).
Nerdel, F. et al., Chem.Ber., vol. 100, pp. 720–735 (1967).
Balog, A. et al., Angew.Chem.Int.Ed.Engl., vol. 35, No. 23/24, pp. 2801–2803 (1997).
Meng, D. et al., J.Am.Chem.Soc., vol. 119, No. 11, pp. 2733–2734 (1997).
Taylor, R.E. et al., Tetrahedron Letters, vol. 38, No. 12, pp. 2061–2064 (1997).
Yang, Z. et al., Angew.Chem.Int.Ed.Engl., vol. 36, No. 1/2, pp. 166–168 (1997).
Blechert, S. et al., Liebigs Ann.Chem., pp. 2135–2140 (1996).
Meng, D. et al., J.Org.Chem., vol. 61, No. 23, pp. 7998–7999 (1996).
Bertinato, P. et al., J.Org.Chem., vol. 61, No. 23, pp. 8000–8001 (1996).
Nicolaou, K.C. et al., Angew.Chem.Int.Ed.Engl., vol. 35, No. 20, pp. 2399–2401 (1996).
Meng et al., J.Am.Chem.Society, vol. 119, pp. 10073–10092 (1997).
Nicolaou et al., Nature, vol. 387, pp. 268–272 (1997).
Nicolaou et al., J.Am.Chem.Soc., vol. 119, pp. 7974–7991 (1997).
Balog et al., Tetrahedron Lett., vol. 38, No. 26, pp. 4529–4532 (1997).
Su et al., Angew.Chem.Int.Ed.Engl., vol. 36, No. 19, pp. 2093–2096 (1997).

*Primary Examiner*—Joseph K. McKane
*Attorney, Agent, or Firm*—Joseph J. Borovian

[57] ABSTRACT

The invention relates to a process for the production of epothilones and intermediate products within the process.

Epothilones A and B are natural substances, which can be produced by microorganisms, and the taxols have similar properties and are thus of particular interest in pharmaceutical chemistry.

1 Claim, No Drawings

INTERMEDIATES IN THE PROCESS FOR PREPARING EPOTHILONES

This is a divisional of U.S. application Ser. No. 08/921,512, filed Sep. 2, 1997, now issued as U.S. Pat. No. 5,969,145, now allowed, which application claims the benefit of provisional application 60/027,480, filed Sep. 26, 1996.

BACKGROUND OF THE INVENTION

The invention relates to a process for the production of epothilones and intermediate products within the process.

Epothilones 1 (DE 41 38 042) represent a new class of tubulin-stabilizing natural substances with taxol-like action. Bollag, *Cancer Research*, 1995, Bd. 55, pp. 2325–2333. Their cytotoxic action with regard to pharmaceutical agent-resistant tumor cell lines is of especially great importance for use in cancer treatment [G. Höfle, N. Bedorf, H. Steinmetz, D. Schomburg, K. Gerth, H. Reichenbach Angew. Chem. [Applied Chemistry] 1996, 108, 1671; Angew. Chem. Int. Ed. Engl. 1996, 35, 1567; D. Schinzer "Epothilones—New Promising Microtubule-Stabilizing Natural Products with Taxol-like Biological Activity," Eur. Chem. Chron. 1996, 1, 7; D. M. Bollag, P. A. McQueney, J. Zhu, O. Hensens, L. Koupal, J. Liesch, M. Goetz, E. Lazarides, C. M. Woods, Cancer Res. 1995, 55, 2325].

Epothilones 1 (A:R=H, B:R=Me) were recently isolated from myxobacteria and are accessible by fermentation. Because of their very advantageous biological properties, the synthesis of epothilones is of greatest importance.

SUMMARY OF THE INVENTION

The object of the invention is the total synthesis of epothilones 1A and B.

Diagram 1. Retrosynthetic analysis
(D. Schinzer, A. Limberg, O. M. Böhm, Chem. Eur. J. 1996, 2, 1477).

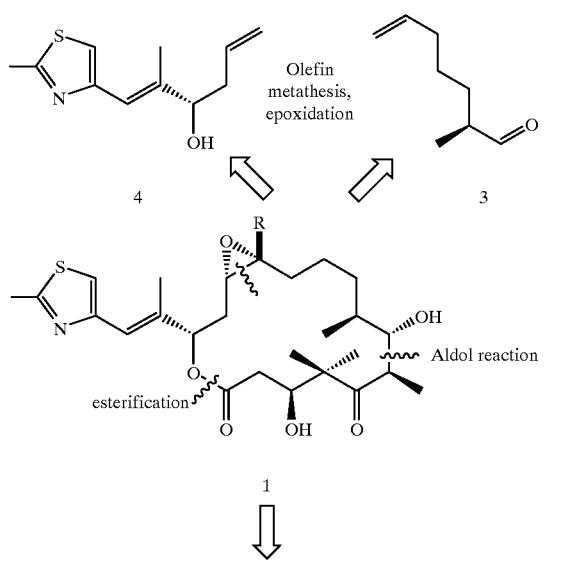

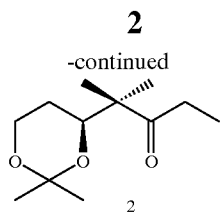

It has now been determined that Epothilones 1 are accessible in a convergent reaction from three components 2, 3 and 4. As the retrosynthesis in diagram 1 shows, components 2 and 3 are linked in a stereoselective aldol reaction. Esterification with fragment 4 yields the almost completely functionalized fragment 17 (below), which is cyclized in ring-closure metathesis to form deoxy-epothilone 19a (below). A final epoxidation ultimately yields 1. A key step in the synthesis is the stereoselective aldol reaction of fragments 2 and 3 (accessible from commercially available heptenoic acid). Under kinetically controlled reaction conditions in the presence of LDA, only desired compound 5 with the four correctly placed asymmetric centers is obtained in 70% yield. Owing to double stereo-differentiation, this is a case of chiral overmodulation of the preferred Cram-selectivity of aldehyde 3 since both reactants are used in optically active form.

The invention thus relates to a process for the production of epothilone A or B of general formula 1

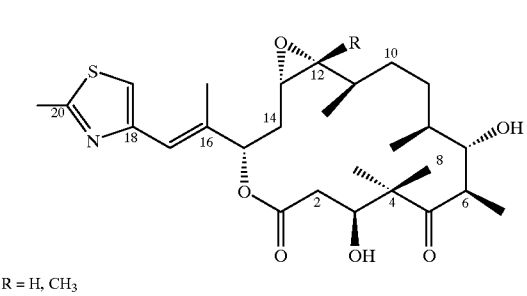

R = H, CH$_3$ in which R=hydrogen (A) or a methyl group (B), whereby a thiazole alkyldiene-alcohol derivative of formula 4

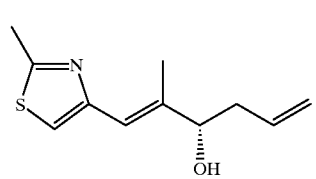

is esterified with a carboxylic acid of general formula 9a

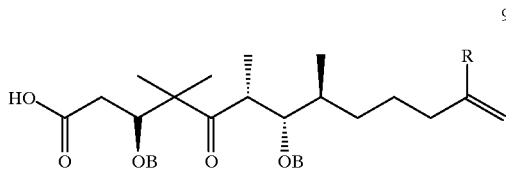

in which
B=benzyl, tetrahydropyranyl and/or a silyl protective group and
R=hydrogen or methyl, the esters that are obtained are cyclized by means of olefin metathesis in the presence of a noble metal catalyst, the hydroxyl protective groups are optionally cleaved, the 12,13-double bond that is newly produced is epoxidized, and optionally the hydroxyl protective groups are cleaved. Reaction conditions and other relevant parameters can be easily, routinely determined by one of ordinary skill in the art in view of the foregoing information, and the representative examples contained herein.

As silyl protective groups B, all different trialkyl- or diaryl-alkyl-silyl protective groups, especially the tert-butyl-dimethyl-, trimethylsilyl- and diphenyl-tert-butyl-silyl groups, are suitable.

Derivatives 4a and 9a are esterified, preferably by using DCCI/DMAP, and the ester that is thus obtained with the two terminal alkene groups is cyclized by olefin metathesis, preferably by using RuCl$_2$ (=CHPh)(PCy$_3$)$_2$, Ph=phenyl, Cy=cyclohexyl, (Grubbs catalyst) (J. Org. Chem. 1996, 61, 3942–3943; Tetrahedron 1996, 52, 7251–7264; J. Am. Chem. Soc., 1995, 117, 12364–12365; J. Am. Chem. Soc., 1995, 117, 2943–2944 and Tetrahedron Lett.; 1994, 35, 3191–3194, J. Am. Chem. Soc., 1996, 118, 6634–6640 and J. Am. Chem. Soc., 1995, 118, 100–110.

The epoxidation of the double bond that is newly produced is carried out preferably by means of peracid, e.g., perchloric acid, or peroxide, e.g., cumene hydroperoxide or dimethyl dioxiran.

The invention additionally comprises deoxy-epothilones according to general formula 19a

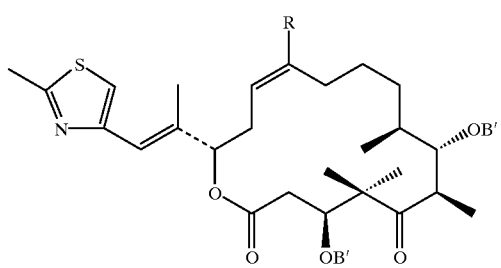

19a in which
B'=hydrogen, benzyl, p-methoxybenzyl, tetrahydropyranyl and/or a silyl protective group(s) and
R=hydrogen or methyl,
(2-(2,2-dimethyl-[1,3]dioxan-4-yl)-2-methyl-pentan-3-one) 2,

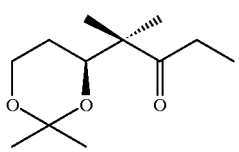

2

2-methyl-6-heptenal 3,

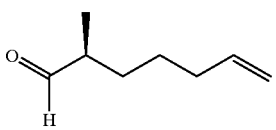

3

2,6-dimethyl-6-heptenal 3a,

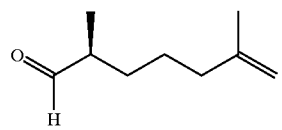

3a compounds of general formula 9a

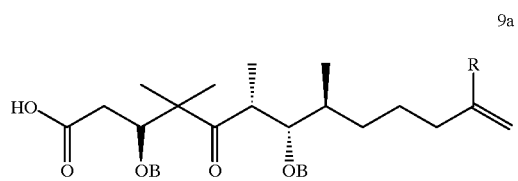

9a in which each

B independently=benzyl, tetrahydropyranyl and/or a silyl protective group(s) and
R=hydrogen or methyl, and compounds of general formula 4a

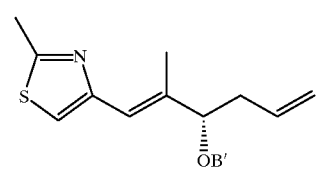

4a in which

B'=hydrogen, benzyl, p-methoxybenzyl, tetrahydropyranyl or a silyl protective group and
(4S,6S)-2-(2,2-dimethyl-[1,3] dioxan-4-yl)-5-hydroxy-2,4,6-trimethyl-undecan-3-one 5.

Epothilones 1 can be used to treat cancers as disclosed in Bollag, supra, in analogy to taxol.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German applications No. 196 36.343.8, filed Aug. 30, 1996; 196 45 361.5, filed Oct. 28, 1996; and 196 45 362.3, filed Oct. 28, 10 1996, is hereby incorporated by reference.

Diagram 2: Production of Compound 9:

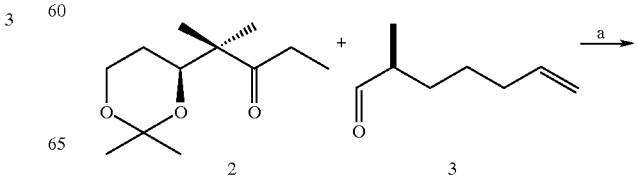

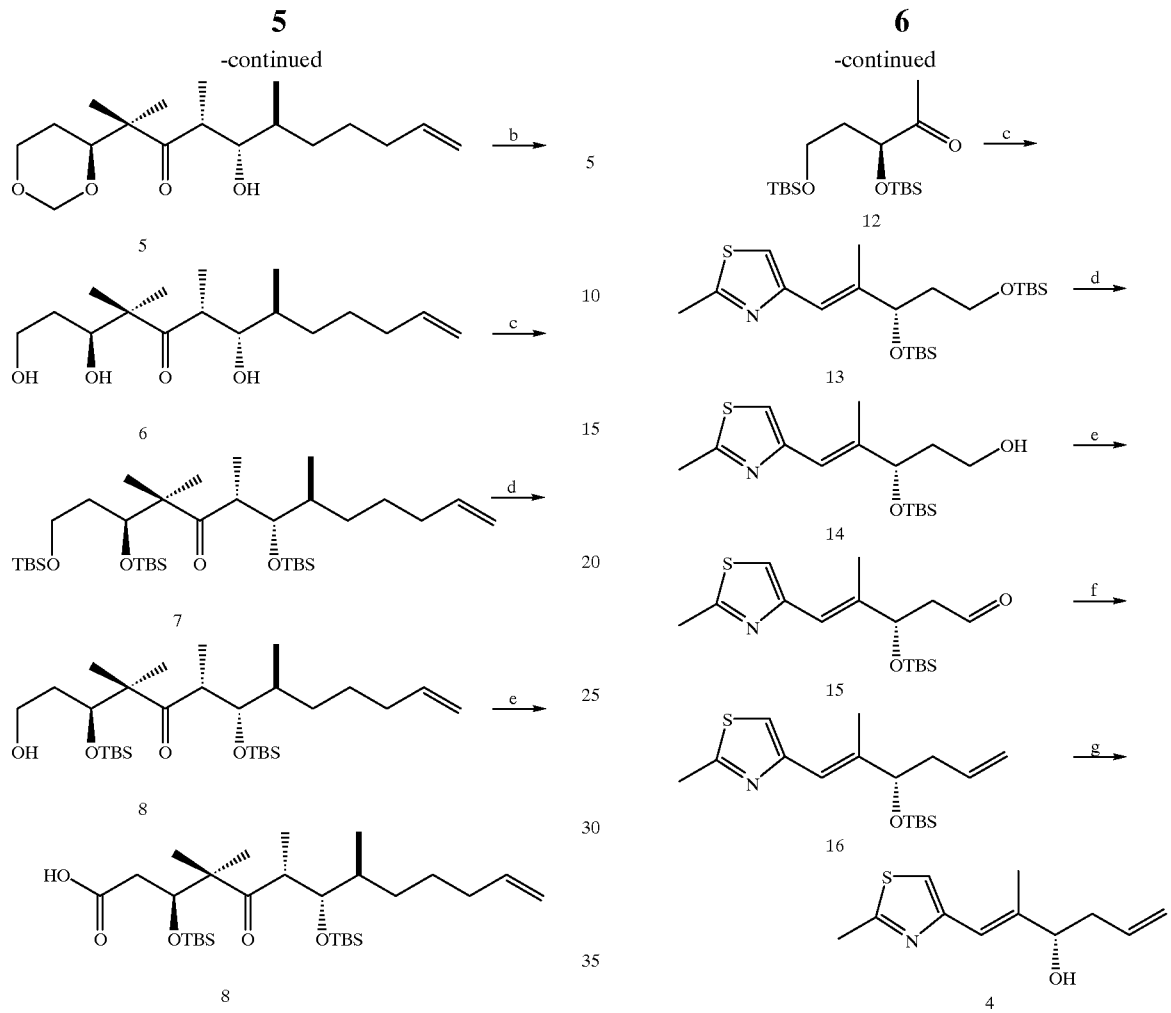

Representative reaction conditions: a) LDA, THF, −78° C., 70%; b) pyridinium-p-toluenesulfonate (PPTS), MeOH, RT [room temperature], 36 hours, 88%; c) 12 equivalents of tBuMe$_2$SiOTf (Tf=trifluoromethanesulfonate), 6 equivalents of 2,6-lutidine, CH$_2$Cl$_2$, −78° C., 96%; d) 0.2 equivalent of CSA (camphorsulfonic acid), MeOH, CH$_2$Cl$_2$, 0° C., 5 hours, 82%; e) 11 equivalents of pyridinium dichromate (PDC), DMF, RT, 36 hours, 79%.

The cleavage of acetonide 5 to triol 6 can be carried out readily in the presence of pyridinium-p-toluenesulfonate (PPTS). Subsequent trisilylation with TBSOTf and lutidine as an auxiliary base yields desired compound 7. To make possible oxidation into acid 9, the primary silyl group must be selectively cleaved. This can be done readily in the presence of camphorsulfonic acid (CSA) and generates compound 8. Subsequent oxidation with pyridinium dichromate (PDC) produces fragment 9, which represents the C1–C12 subunit of 1.

Diagram 3: Production of Compound 4

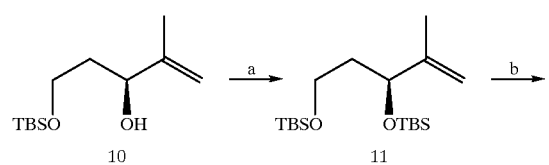

a) TBSCl, imidazole, DMF, RT, 10 hours, 98%; b) O$_3$, PPh$_3$, CH$_2$Cl$_2$, −78° C., 70%; c) 1.5 equivalents of diethyl (2-methylthiazol-4-yl)methanephosphonate, nBuLi, THF, −78° C. →RT, 75%; d) HF, MeCN, several glass fragments, 0° C., 87%; e) Dess-Martin periodinane, CH$_2$Cl$_2$, RT, 1 hour, 78%; f) 1.85 equivalents of PPh$_3$MeBr/NaNH$_2$, THF, RT, 20 minutes, 83%; g) 2.5 equivalents of tetrabutylammonium fluoride (TBAF), 4 Å molecular sieve, THF, −78° C.→RT, 99%.

(S)-Alcohol 10, which was accessible via a Sharpless resolution [D. Schinzer, A. Limberg, O. M. Böhm, Chem. Eur. J. 1996, 2, 1477], was first silylated with TBSCl, then ozonized into methylketone 12 and reacted in a stereoselective Horner-Wadsworth-Emmons reaction into tricyclic olefin 13. Selective desilylation with HF in acetonitrile yields compound 14. Desilylation into 14 works in the presence of a few glass fragments; obviously, the reaction is catalyzed by H$_2$SiF$_6$. Dess-Martin oxidation, followed by Wittig olefination, generates compound 16, which yields segment 4 in a final desilylation with TBAF in THF.

The esterification of components 9 and 4 in the presence of DCC and 4-DMAP produces compound 17, which is isolated in stereochemically homogeneous form.

Diagram 4: Production of Epothilone C (compound 19) and Epothilone A:1

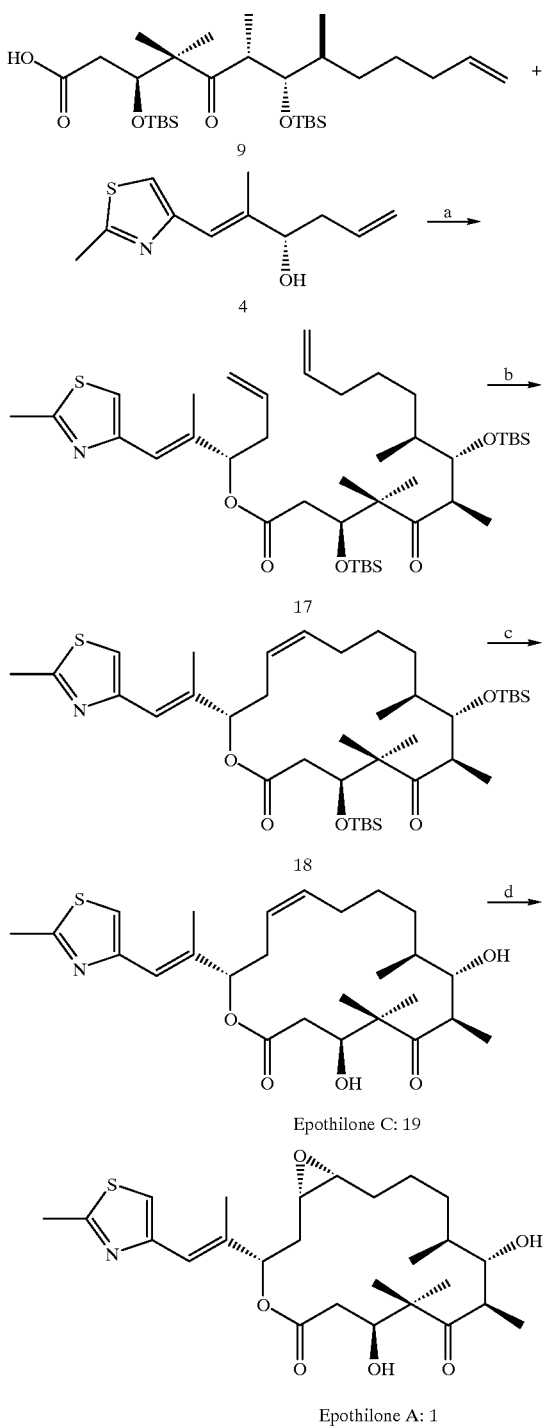

Epothilone C: 19

Epothilone A: 1 a) 1.3 equivalents of dicyclohexylcarbodiimide (DCC), 0.2 equivalent of 4-dimethylaminopyridine (4-DMAP), $CH_2Cl_2$, RT, 12 hours, 80%; b) $Cl_2[RuCHPh](PCy_3)_2$, $CH_2Cl_2$, RT, 12 hours, 94% (Z:E=1:1); c) HF, MeCN, $Et_2O$, RT, 12 hours, 65%, d) dimethyl dioxiran, $CH_2Cl_2$, −35° C., 2 hours, 48%.

Ring-closure metathesis with $Cl_2[RuCHPh[(PCy_3)_2$ in $CH_2Cl_2$ yields 18 as a diastereomeric mixture (Z:E=1:1) in 94% yield. Desilylation with HF in acetonitrile/ether to form 19 and regioselective and stereoselective epoxidation with dimethyl dioxiran to 1 form the end of the total synthesis. The main product of this reaction is (−)-epothilone A, which is chromatographically and spectroscopically identical to an authenticated sample.

Overall, a strictly convergent synthesis was described, which keeps open many options to analogues; this is important with respect to biological activity. The entire synthesis makes do with one protective group type (TBS), which is linked or cleaved in selective reactions. The stereoselective aldol reaction is high and represents an additional impressive example of the chiral overmodulation of aldehyde selectivity with a chiral enolate. Ring-closure metathesis into 18 is possible in 94% isolated yield, yielding a 1:1 mixture of Z and E isomers. The considerably more biologically active epothilone B 1 (R=Me) is accessible via the same method of production.

Production of 2

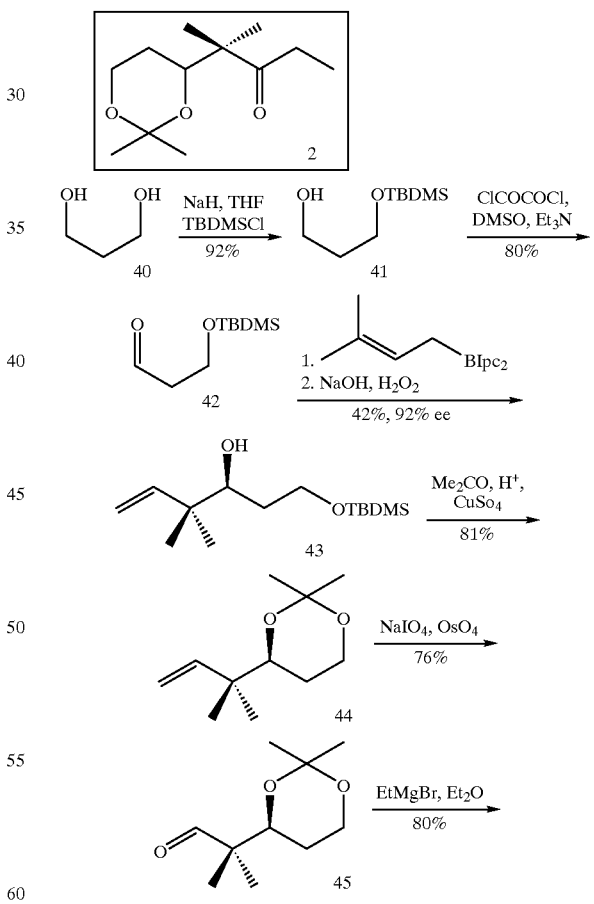

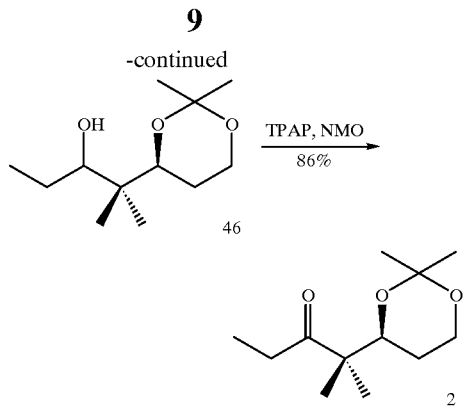

Operating instructions for synthesis of segment 2 (2-(2,2-Dimethyl-[1,3]dioxan-4-yl)-2-methyl-pentan-3-one) (D. Schinzer, A. Limberg, O. M. Böhm, Chem. Eur. J. 1996, 2, 1477).

3-[(tert-Butyldimethylsilyl)oxy]propanal 42 is produced using propane-1,3-diol 40 as a starting material by monosilylation into 3-[(tert-butyldimethylsilyl)oxy]-1-propanol 41 being done first according to a method of P. G. McDougal, J. G. Rico, Y. Oh, B. D. Condon, J. Org. Chem. 1986, 51, 3388–3390, which then is oxidized to aldehyde 42 with DMSO/oxalyl chloride (A. Jenmalm, W. Berts, Y. Li, K. Luthmann, I. Csöregh, U. Hacksell, J. Org. Chem. 1994, 59, 1139–1148).

Production of 1-[(tert-butyldimethylsilyl)oxy]-4,4-dimethyl-hex-5-en-3-ol 43
(H. C. Brown, P. K. Jadhav, Tetrahedron Lett. 1984, 25, 1215–1218; P. K. Jadhav, K. S. Bhat and P. Thirumalai, H. C. Brown, J. Org. Chem. 1986, 51, 432–439)

500 mg (7.34 mmol, 1 equivalent) of 3-methyl-1,2-butadiene is slowly added in drops to a suspension, cooled to −25° C., of Ipc$_2$BH (7.34 mmol, produced from (−)-α-pinene [99%, 97% ee] H. C. Brown, M. C. Desai, P. K. Jadhav, J. Org. Chem. 1982, 47, 5065–5069; H. C. Brown, B. Singaram, J. Org. Chem. 1984, 49, 945–947, also available from ALDRICH) in 2.6 ml of THF, and the reaction mixture is stirred for 6 hours at −25° C. The THF is then pumped off at room temperature (14 mm of Hg/1 hour), (0.5 mm/2 hours), and the residue is dissolved in 10.5 ml of diethyl ether. The solution is cooled to −78° C., and 1.382 g (7.34 mmol, 1 equivalent) of aldehyde 42 is added in drops. It is dissolved while being stirred for 12 hours at −78° C. and then allowed to heat to room temperature. The reaction mixture is mixed with 10.7 ml of 3N NaOH solution, then heated under reflux with 4.4 ml of 30% H$_2$O$_2$ solution for 2 hours. The organic phase is separated, washed with 15 ml of H$_2$O and 15 ml of saturated NaCl solution, dried on MgSO$_4$ and concentrated by evaporation. The residue is purified by column chromatography with pentane:ether=2:1, and 800 mg (3.098 mmol) of alcohol 43, corresponding to a yield of 42%, is obtained.

The determination of excess enantiomer is done by GC-analytic examination of the diastereomeric compounds, which are obtained with esterification of the alcohol with (1R)-(−)-camphanic chloride, and this yielded an ee-value of 92%.

General Data: $C_{14}H_{30}O_2Si$, MW=258.47 g/mol
$^{13}$C-NMR (100 MHz, CDCl$_3$): 145.69 (d), 112.27 (t), 78.52 (d), 63.29 (t), 41.19 (s), 33.39 (t), 25.89 (q), 22.85 (q), 22.43 (q), 18.17 (s), −5.52 (q)

Production of 4(1,1-dimethyl-allyl)-2,2-dimethyl-[1,3]dioxane 44
278 mg (1.076 mmol) of alcohol 43 is dissolved in 13 ml of acetone, and 200 mg (2.51 mmol, 2.3 equivalents) of anhydrous CuSO$_4$ is added. Then, 40 drops of a solution of 0.1 ml of glacial acetic acid in 1 ml of CH$_2$Cl$_2$ are added and stirred for 12 hours at room temperature. If more educt can be detected by thin-layer chromatography, additional acid solution is added until the reaction is completed. For working-up, the reaction mixture is poured onto saturated NaHCO$_3$ solution, and the aqueous phase is extracted with DE. The combined organic phases are dried on MgSO$_4$ and concentrated by evaporation in a rotary evaporator. The residue is purified by column chromatography with pentane:ether=2:1. 161 mg (0.87 mmol) of acetonide 44 corresponding to a yield of 81% is obtained.

General Data: $C_{11}H_{20}O_2$, MW=184.28 g/mol
$^{13}$C-NMR (100 MHz, CDCl$_3$): 145.10 (d), 111.88 (t), 98.19 (s), 75.32 (d), 60.10 (t), 39.97 (s), 29.80 (q), 25.88 (t), 22.86 (q), 22.45 (q), 19.11 (q)

Production of 2-(2,2-dimethyl-[1,3]dioxan-4-yl)-2-methyl-propionaldehyde 45
286 mg (1.55 mmol) of acetonide 44 is dissolved in 18 ml of THF, and 14 ml of aqueous phosphate buffer at pH 7 is added. 400 μl (0.031 mol, 0.02 equivalent) of OsO$_4$ solution (2.5% in tert-butanol) is added in drops to the reaction mixture that is stirred vigorously. After 10 minutes, 996 mg (4.656 mmol, 3 equivalents) of NaIO$_4$ is added in portions over a period of 20 minutes. The mixture is stirred vigorously at room temperature and, after 24 and 48 hours in each case, another 332 mg (1.55 mmol, 2×1.0 equivalents each) of NaIO$_4$ is added. After 55 hours, the phases are separated, the aqueous phase is extracted with ether, the combined organic phases are dried on MgSO$_4$ and concentrated by evaporation. The residue is purified by column chromatography with pentane:DE=1:1. 221 mg (1.19 mmol) of aldehyde 45 corresponding to a yield of 76% is obtained.

General Data: $C_{10}H_{18}O_3$, MW=186.25 g/mol
$^{13}$C-NMR (100 MHz, CDCl$_3$): 206.09 (d), 98.43 (s), 72.94 (d), 59.75 (t), 48.84 (s), 29.57 (q), 25.57 (t), 18.96 (q), 18.62 (q), 16.46 (q)

Production of 2-(2,2-dimethyl-[1,3]dioxan-4yl)-2-methyl-pentan-3-ol 46
A solution of 268 mg (1.44 mmol) of aldehyde 45 in 4 ml of diethyl ether is mixed at 0° C. with 528 μl (1.58 mmol, 1.1 equivalents) of a 3 M solution of EtMgBr in ether. It is allowed to stir for 2 hours at 0° C., heated to room temperature and allowed to stir for another hour. For working-up, it is mixed with saturated aqueous NH$_4$Cl solution, and then water is added steadily until the precipitate goes into solution. The aqueous phase is extracted with ether, the combined organic phases are dried on MgSO$_4$ and concentrated by evaporation. The residue is purified by column chromatography with pentane:ether=1:1. 251 mg (1.16 mmol) of alcohol 46, corresponding to a yield of 80%, is obtained.

General Data: $C_{12}H_{24}O_3$, MW=216.31 g/mol
$^{13}$C-NMR (100MHz, C$_6$D$_6$): 98.41 (s), 79.95 (d), 76.65 (d), 60.10 (t), 40.60 (s),
Diastereomer 1: 30.04 (q), 25.73 (t), 24.64 (t), 20.03 (q), 19.25 (q), 15.99 (q), 11.67 (q)
$^{13}$C-NMR (100 MHz, C$_6$D$_6$): 98.57 (s), 78.85 (d), 76.46 (d), 60.08 (t), 39.93 (s),
Diastereomer 2: 30.02 (q), 25.41 (t), 25.08 (t), 20.85 (q), 20.30 (q), 18.90 (q), 11.95 (q)

Production of 2-(2,2-dimethyl-[1,3]dioxan-4yl)-2-methyl-pentan-3-one 2: W. P. Griffith, S. V. Ley, G. P. Whitcombe, A. D. White, J. Chem. Soc., Chem. Commun. 1987, 1625–1627.

70 mg (0.32 mmol) of alcohol 46 is dissolved in 5 ml of CH$_2$Cl$_2$, and 6 4Å molecular sieve spheres and 66 mg (0.48 mmol, 1.5 equivalents) of 4-methylmorpholine N-oxide (NMO) are added. After 10 minutes of stirring, 6 mg of tetrapropylammonium-perruthenate (VII) (TPAP) (0.016 mmol, 0.05 equivalent) is added and stirred for 4 hours at room temperature. Then, the reaction mixture is concentrated by evaporation in a rotary evaporator and directly purified by column chromatography with pentane:ether=1:1. 60 mg (0.28 mmol) of ethyl ketone 2, corresponding to a yield of 86%, is obtained.

General Data: $C_{12}H_{22}O_3$, MW=214.30 g/mol $^{13}$C-NMR (100 MHz, $C_6D_6$): 213.23 (s), 98.42 (s), 74.18 (d), 59.82(t), 50.44 (s), 31.70 (t), 30.03 (q), 25.55 (t), 20.97 (q), 19.35 (q), 19.04 (q), 8.16 (q)

Synthesis of 2-methyl-6-heptenal 3 and 3a

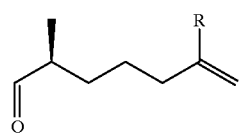

3 R = H
3a R = Me

The production is carried out in a way similar to the synthesis of 6-tert-butyldimethylsilyloxy-2-methyl-hexanol 50 [D. Schinzer, A. Limberg, O. M. Böhm, Chem. Eur. J. 1996, 2, 1477].

Synthesis of segment 4:

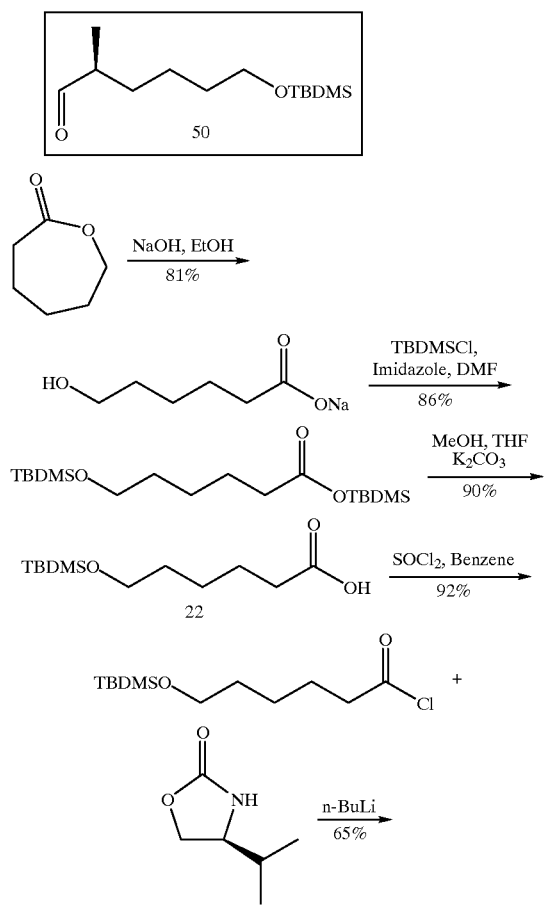

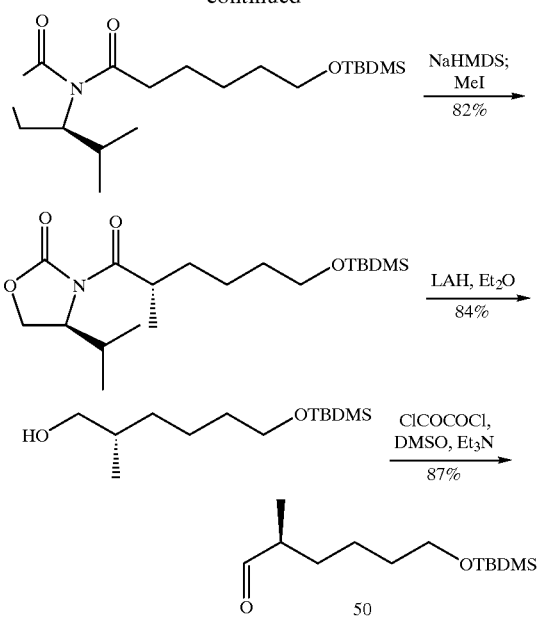

Operating instructions for the production of segment 3:

Sodium-6-hydroxyhexanoate is produced according to instructions from Wulff, Krüger and Röhle Chem. Ber. 1971, 104, 1387–1399 from G-caprolactone.

Production of 6-[(tert-butyldimethylsilyl)oxy]-hexanoic acid silyl ester

A mixture of 2.00 g (12.97 mmol) of sodium-6-hydroxyhexanoate, 25 ml of DMF, 5.87 g (38.93 mmol, 3 equivalents) of TBDMSCl and 5.3 g (77.85 mmol, 6 equivalents) of imidazole is stirred for 48 hours at room temperature. The reaction mixture is flash-filtered and then purified by column chromatography with pentane:DE=4:1. 3.99 g (11.1 mmol) of the bissilylated compound 6-[(tert-butyldimethyl-silyl)oxy]-hexanoic acid silyl ester, corresponding to a yield of 85%, is obtained.

General Data: $C_{18}H_{40}O_3Si_2$, MW=360.69 g/mol $^{13}$C-NMR (100 MHz, $CDCl_3$): 174.17 (s), 63.00 (t), 36.02 (t), 32.53 (t), 25.95 (q), 25.55 (q), 25.40 (t), 24.91 (t), 18.33 (s), 17.57 (s), −4.83 (q), −5.32 (q)

Production of 6[(tert-butyldimethylsilyl)oxy]-hexanoic acid according to D. R. Morton, J. L. Thompson, J. Org. Chem. 1978, 43, 2102–2106.

A solution of 3.25 g (9.02 mmol) of the bissilylated compound 6-[(tert-butyldimethyl-silyl)oxy]-hexanoic acid silyl ester in 130 ml of methanol and 44 ml of ThF is mixed with a solution of 4.4 g (31.8 mmol, 3.5 equivalents) of $K_2CO_3$ in 44 ml of $H_2O$, and it is stirred for 1 hour at room temperature. Then, the volume of reaction solution is reduced to one-fourth in a vacuum. It is diluted with 130 ml of saturated NaCl solution and set at pH 4–5 with 1 M $KHSO_4$ solution. It is extracted with diethyl ether. The combined organic phases are dried on $MgSO_4$, and the solvent is distilled off in a rotary evaporator. 2.01 g (8.17 mmol) of 6-[(tert-butyldimethylsilyl)oxy]-hexanoic acid, corresponding to a yield of 90%, is obtained.

General Data: $C_{12}H_{26}O_3Si$, MW=246.42 g/mol $^{13}$C-NMR (100 MHz, $CDCl_3$): 180.09 (s), 62.90 (t), 34.05 (t), 32.37 (t), 25.93 (q), 25.31 (t), 24.46 (t), 18.32 (s), −5.33 (q)

Production of 6-[(tert-butyldimethylsilyl)oxy]-hexanoyl chloride

J. Tanaka, Bull. Chem. Jpn. 1992, 65, 2851–2853.

A solution of 0.5 g (2.03 mmol) of 6-[(tert-butyldimethylsilyl)oxy]-hexanoic acid in 4 ml of benzene is mixed with 362 mg (3.04 mmol, 1.5 equivalents) of $SOCl_2$ and heated under reflux for 2 hours. It is allowed to cool, and the solvent is distilled off in a rotary evaporator. To remove excess $SOCl_2$ from the reaction mixture, the residue is mixed again with benzene and again distilled off. 494 mg (1.865 mmol, 92%) of the 6-[(tert-butyldimethylsilyl)oxy]-hexanoyl chloride is obtained. This crude product is further reacted without purification and characterization.
*(S)-4-Isopropyl-3-propenoyl-oxazolidin-2-one 20

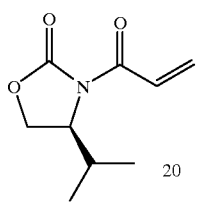

Production in a way similar to: D. A. Evans, K. T. Chapman, J. Bisha J. Am. Chem. Soc. 1988, 110, 1238; A Studer, T. Hintermann, D. Seebach Helv. Chim. Acta 1995, 78, 1185. 6.88 ml of a 1.6M solution of n-BuLi in hexane (11.0 mmol) is slowly added to a solution of 1.299 g (10.0 mmol) of (S)-4-isopropyl-oxazolidin-2-one in 15 ml of absolute THF at −78° C. The solution is stirred for 30 minutes at −78° C.; 1.22 ml (15.0 mmol) of acrylic acid chloride is added drop by drop; it is allowed to reach room temperature and hydrolyzed with 50 ml of saturated $NH_4Cl$ solution. It is extracted three times with 50 ml of $Et_2O$ each. After drying on $MgSO_4$, the solvent is removed. By flash-chromatographic purification with pentane/$Et_2O$ (10:1), 1.63 g (8.9 mmol, 89%) of 20 is obtained.
(S)-4-Isopropyl-3-(6-methylhept-6-enoyl)-oxazolidin-2-one 21a

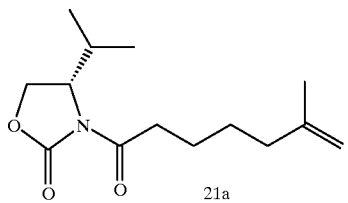

Production in a way similar to:
A. Studer, T. Hintermann, D. Seebach Helv. Chim. Acta 1995, 78, 1185

47 mg (1.9 mmol) of Mg chips is stirred at room temperature (or while being heated intermittently) in 1.5 ml of absolute THF with 283 mg (1.9 mmol) of 4-bromo-2-methyl-1-butene, until all Mg has gone into solution. This Grignard solution is mixed at −30° C. with a suspension of 197 mg (1.00 mmol) of CuBr—$Me_2S$ in 1.5 ml of absolute THF. It is stirred for 30 minutes at this temperature; 117 mg (0.64 mmol) of 20 on 2 ml of absolute THF is added; it is stirred for 16 hours at −10° C. and hydrolyzed with 10 ml of saturated $NH_4Cl$ solution. It is extracted three times with 20 ml of $Et_2O$ each. After drying on $MgSO_4$, the solvent is removed. By flash-chromatographic purification with pentane/$Et_2O$ (15:1), 128 mg (0.51 mmol, 79%) of 21a is obtained.
Hept-6-enoyl chloride
A solution of 2.58 g (20.13 mmol) of hept-6-enoic acid in 10 ml of $CH_2Cl_2$ is mixed with 5.11 g (40.26 mmol, 2 equivalents) of oxalyl chloride, then stirred for 1 hour at room temperature and for 1 hour at 40° C. It is allowed to cool, and the solvent is distilled off at 5 mbar. 2.95 g (20.13 mmol, 100%) of the acid chloride is obtained. This crude product is reacted without further purification.
General Data: $C_7H_{11}ClO$, MW=146.62 g/mol
(S)-3-Hept-6-enoyl-4-isopropyl-oxazolidin-2-one 21

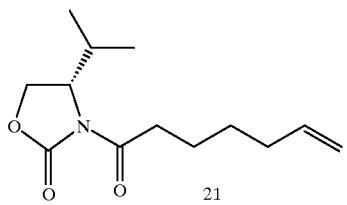

A. Gonzalez, Synth. Comm. 1991, 21, 1353–1360
A solution of 2.08 g (16.10 mmol, 1 equivalent) of (4S)-4-isopropyl-oxazolidin-2-one in 15 ml of THF is cooled to −78° C. and mixed drop by drop with 11.6 ml (18.52 mmol, 1.15 equivalents) of a 1.6 M solution of n-BuLi solution in hexane. Then, a solution of 2.95 g (20.13 mmol, 1.25 equivalents) of hept-6-enoyl chloride in 10 ml of THF is added at −78° C. It is allowed to heat to room temperature, and the reaction solution is poured onto saturated NaCl solution. The aqueous phase is extracted with ether, the combined organic phases are dried on $MgSO_4$, and the solvent is distilled off in a rotary evaporator. The residue is purified by column chromatography with PE:DE=3:1. 3.55 g (14.82 mmol, 92%) of oxazolidinone 21 is obtained as a colorless oil.
General Data: $C_{13}H_{21}NO_3$, MW=239.31 g/mol
(4S,2'S)4Isopropyl-3-(2-methyl-hept-6-enoyl)-oxazolidin-2-one 22analogously to the production of 25 and
(4S,2'S)-4-isopropyl-3-(2,6-dimethylhept-6-enoyl)-oxazolidin-2-one 22a

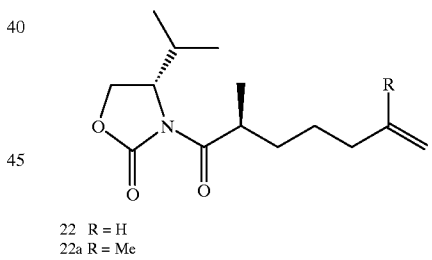

22 R = H
22a R = Me

D. A. Evans, A. E. Weber J. Am. Chem. Soc. 1986, 108, 6757–6761
9.02 ml (9.02 mmol, 1.15 equivalents) of a 1 M solution of NaHMDS in THF is cooled to −78° C. and mixed drop by drop with a solution, cooled to 0° C., of 1.88 g (7.84 mmol) of oxazolidinone 21 in 8 ml of THF. It is allowed to stir for 1 hour at −78° C., 5.57 g (39.22 mmol, 5 equivalents) of MeI, dissolved in 2 ml of THF, is added, and allowed to stir for 4 hours at −78° C. Then, it is quenched with saturated $NH_4Cl$ solution, extracted with diethyl ether, dried on $MgSO_4$ and concentrated by evaporation. The residue is purified by column chromatography with PE:DE=4:1. 1.51 g (5.96 mmol, 76%) of methylated compound 22 is obtained.
General Data: $C_{14}H_{23}NO_3$, MW=253.34 g/mol
Compound 22a is produced analogously. 1.56 g (5.84 mmol, 73%) of 22a is obtained from 2.03 g (8.0 mmol) of 21a.

(S)-2-Methyl-hept-6-en-1-ol 23 and
(S)-2,6-dimethylhept-6-en-1-ol 23a

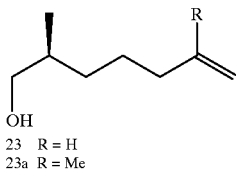

23  R = H
23a R = Me

D. A. Evans, A. E. Weber J. Am. Chem. Soc. 1986, 108, 6757–6761

5.83 ml (5.83 mmol, 2 equivalents) of a 1 M suspension of LAH in diethyl ether is slowly added to a solution, cooled to 0° C., of 738 mg (2.91 mmol) of the methylated compound 22 in 10 ml of diethyl ether. It is quenched by the addition of 221 ml of water, 221 ml of 15% aqueous NaOH solution and 663 ml of water. Then, it is flash-filtered on Celite with diethyl ether and purified by column chromatography with pentane:DE=3:1. 299 mg (2.33 mmol, 80%) of alcohol 23 is obtained as a colorless liquid.

General Data: $C_8H_{16}O$, MW=128.21 g/mol

Compound 23a is produced analogously. 331 mg (2.32 mmol, 83%) of 23a is obtained from 748 mg (2.80 mmol) of 22a.

(S)-2-Methyl-hept-6enal 3 and (S)-2,6dimethylhept-6-enal 3a

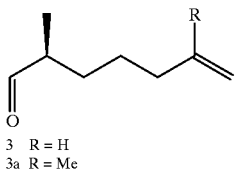

3  R = H
3a R = Me

A solution of 295 mg of alcohol 23 (2.30 mmol) in 5 ml of $CH_2Cl_2$ is mixed with 1.269 g (2.99 mmol, 1.3 equivalents) of Dess-Martin periodinane (1,1,1-triacetoxy-1,1-dihydro-1,2-benzodioxol-3(1H)-one, and it is stirred for 25 minutes at room temperature. For working-up, a volume equivalent of phosphate buffer at pH 7 is added. The aqueous phase is extracted with $CH_2Cl_2$, the combined organic phases are dried on $MgSO_4$, and the solvent is distilled off in a rotary evaporator. The residue is purified by column chromatography with pentane:DE=10:1. 224 mg (1.77 mmol, 77%) of the aldehyde is obtained as a colorless liquid.

General Data: $C_8H_{14}O$, MW=126.20 g/mol

Compound 3a is produced analogously. 199 mg (1.42 mmol, 71%) of 3a is obtained from 284 mg (2.00 mmol) of 23a.

Production of 4:

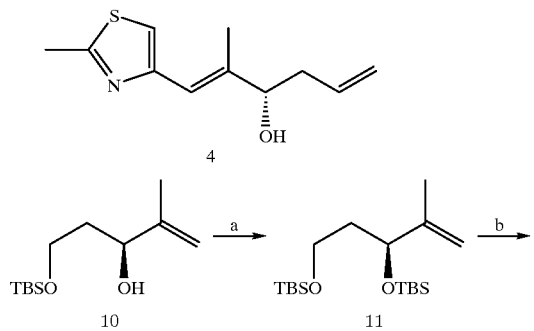

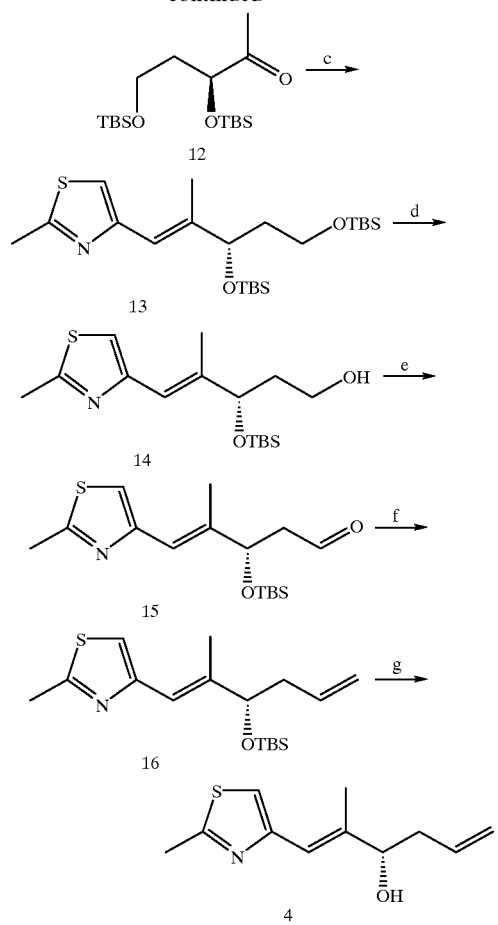

Synthesis of segment 4:
3-[(t-Butyldimethylsilyl)oxy]-propanal

Synthesis by monosilylation of 1,3-propanediol and subsequent Swern oxidation of the 3-[(t-butyldimethylsilyl)oxy]-1-propanol that is produced.

General Data: $C_9H_{20}O_2Si$; MW=188.36; CAS No. [89922-82-7]

$^{13}$C-NMR (100 MHz, $CDCl_3$): d=202.05 (d), 57.42 (t), 46.58 (t), 25.82 (q), 18.23 (s), −5.43 (q)

1-[(t-Butyldimethylsilyl)oxy]-3-hydroxy-4-methyl-4-pentene 10

0.2 ml of 2-bromopropene is added to 443 mg of Mg chips (18.2 mmol) and 1.5 ml of absolute THF under $N_2$, so that the reaction starts quickly. A solution of 1.7 ml of 2-bromopropene (22 mmol altogether) in 6 ml of absolute THF is slowly added in drops while being cooled intermittently, until all Mg chips are dissolved. A solution of 2.862 g of 3-[t-butyldimethylsilyl)oxy]-propanol (15.2 mmol) in 6 ml of absolute THF is added in drops to the mixture that is still warm. It is heated for 6 hours at room temperature. Then, 25 ml of saturated $NH_4Cl$ solution is added to the reaction solution and allowed to stir for 10 minutes. The mixture is poured into 30 ml of saturated $NH_4Cl$ solution and extracted twice with ether. The combined organic phases are washed once each with saturated $NH_4Cl$ solution and saturated NaCl solution. It is dried on $MgSO_4$, concentrated by evaporation in a vacuum and purified by flash chromatography (ether:pentane=1:6).

2.749 g of 10 (11.9 mmol; 79% of theory) is obtained as a colorless oil.

General Data: $C_{12}H_{26}O_2Si$; MW=230.43

$^{13}$C-NMR (100 MHz, CDCl$_3$): d=147.10 (s), 110.39 (t), 75.21 (d), 62.17 (t), 36.79 (t), 25.89 (q), 18.41 (s), −5.49 (q), −5.53 (q)

(S)-1,3-Di-[(tert-butyldimethylsilyloxy)]-4-methyl-4-pentene 11

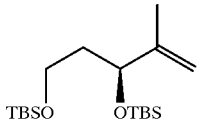

11

946 mg (6.28 mmol, 1.3 equivalents) of tert-butyldimethylchlorosilane is added to a solution of 1.173 g (4.83 mmol) of (S)-1-[(tert-butyldimethylsilyloxy)]-4-methyl-4-penten-3-ol 10and 855 mg (12.56 mmol, 2.6 equivalents) of imidazole in 15.0 ml of absolute DMF. The mixture is stirred for 16 hours at room temperature. It is mixed with 50 ml of an aqueous 1 M KHSO$_4$ solution and extracted four times with 50 ml of Et$_2$O each. The combined ether extracts are dried on MgSO$_4$. After the solvent is distilled off in a vacuum, the residue is flash-chromatographed by a silica gel column with pentane/Et$_2$O (20:1). As an alternative to this aqueous working-up, the reaction mixture can be chromatographed directly. By the two variations of working-up procedure, 1.643 g (4.73 mmol, 98%) of 11 is obtained.

(S)-3,5-Di-[(tert-butyldimethylsilyloxy)]-pentan-2-one 12

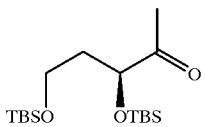

12

Ozone in O$_2$ is directed at −78° C. through a solution of 1.610 g (4.67 mmol) of 11 in 200 ml of absolute dichloromethane (dry ice/acetone-cold bath). When starting compound 11 can no longer be detected by thin-layer chromatography in the solution, 3.89 g (14.83 mmol) of triphenylphosphine is added, and the cold bath is removed. The reaction batch is allowed to come slowly to room temperature, and the solvent is distilled off in a vacuum. Flash chromatography of the residue by a silica gel column with pentane/Et$_2$O (50:1) yields 1.135 g (3.27 mmol, 70%) of 12.

Diethyl-(2-methylthiazol-4-yl)-methanephosphonate

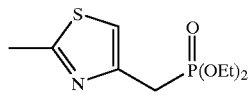

The production is carried out starting from 4-chloromethyl-2-methylthiazole, known in the literature, analogously to the instructions for 4-bromomethyl-2-methylthiazole. 9.971 g (40 mmol, 80%) of diethyl-(2-methylthiazol-4-yl)-methanephosphonate is obtained from 7.381 g (50 mmol) of 4-chloro-methyl-2-methylthiazole.

(S,4E)-4-[3,5-Di-(tert-butyldimethylsilyloxy)-2-methyl-pent-1-enyl]-2-methyl-thiazole 13

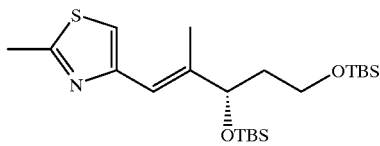

13

2.94 ml of n-BuLi (1.6 M solution in hexane) is added in drops to a solution of 1.170 g (4.70 mmol) of diethyl-(2-methylthiazol-4-yl)-methanephosphonate in 15 ml of absolute THF at −78° C. It is allowed to stir for 45 minutes at −78° C., and then a solution of 1.135 g (3.27 mmol) of 12 in 10 ml of absolute THF is slowly added in drops, allowed to heat to room temperature and stirred for another 12 hours at room temperature. The reaction mixture is mixed with 100 ml of saturated NH$_4$Cl solution and extracted four times with 80 ml of Et$_2$O each. The combined ether extracts are washed with saturated NaCl solution and dried on MgSO$_4$. After the solvent is distilled off in a vacuum, the residue is flash-chromatographed by a silica gel column with pentane/dichloromethane (2:3). 1.090 g (2.47 mmol, 75%) of 13 is obtained.

(S,4E)-3-(tert-Butyldimethylsilyloxy)-4-methyl-5-(2-methyl-thiazol-4-yl)-pent-4-en-1-ol 14

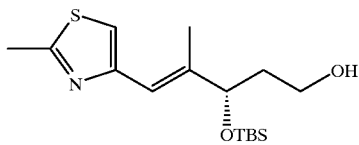

14

A solution of 442 mg (1.0 mmol) of 13 in 40 ml of acetonitrile is mixed at −20° C. drop by drop with 0.45 ml of hydrofluoric acid (40%). After some glass fragments are added or after 0.045 ml of hexafluorosilicic acid (30%) is added, it is stirred at 0° C. until starting compound 13 can no longer be detected by thin-layer chromatography in the solution. The reaction mixture is mixed with 50 ml of saturated NaHCO$_3$ solution and extracted four times with 80 ml of Et$_2$O each. The combined ether extracts are dried on MgSO$_4$. After the solvent is distilled off in a vacuum, the residue is flash-chromatographed by a silica gel column with Et$_2$O. 284 mg (0.87 mmol, 87%) of 14 is obtained.

(S,4E)-3-(tert-Butyldimethylsilyloxy)-4-methyl-5-(2-methyl-thiazol-4-yl)-pent-4-enal

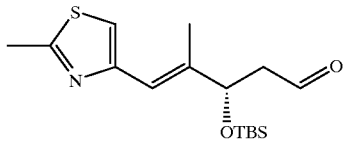

15

A suspension of 478 mg (1.127 mmol, 1.3 equivalents) of Dess-Martin periodinane (1,1,1-triacetoxy-1,1-dihydro-1,2-benzodioxol-3(1H)-one) in 5.6 ml of absolute CH$_2$Cl$_2$ is mixed with a solution of 284 mg (0.87 mmol) of 14 in 5.0 ml of absolute CH$_2$Cl$_2$ and stirred for 60 minutes at room temperature. After the solvent is distilled off in a vacuum, the residue is flash-chromatographed by a silica gel column with pentane/Et$_2$O (4:1). 222 mg (0.68 mmol, 78%) of 15 is obtained.

(S,4E)-4-[3-(tert-Butyldimethylsilyloxy)-2-methyl-hexa-1,5-dienyl]-2-methyl-thiazole 16

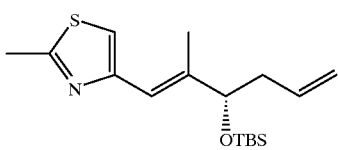

16

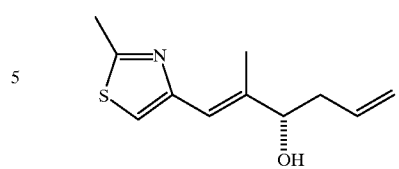

4

440 mg (1.06 mmol, 1.85 equivalents) of a mixture of equimolar amounts of sodium amide and methyltriphenylphosphonium bromide is stirred for 30 minutes at room temperature in 4.0 ml of absolute THF. A solution of 185 mg (0.57 mmol) of 15 in 5.0 ml of absolute THF is added, stirred for another 20 minutes, mixed with 20 ml of saturated NaHCO₃ solution and extracted four times with 30 ml of Et₂O each. The combined ether extracts are dried on MgSO₄. After the solvent is distilled off in a vacuum, the residue is flash-chromatographed by a silica gel column with pentane/Et₂O (20:1). 151 mg (0.47 mmol, 83%) of 16 is obtained.

2-Methyl-1-(2-methyl-thiazol-4-yl)-hexa-1,5-dien-3-ol 4

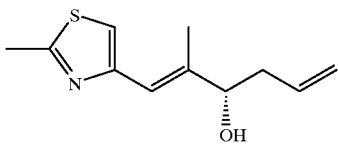

4

1.18 ml (1.18 mmol, 2.5 equivalents) of a 1 M TBAF solution in THF is stirred in 10 ml of absolute THF for 20 minutes with a 4 Å activated molecular sieve at room temperature to bond residual water to the TBAF solution. A solution of 151 mg (0.47 mmol) of 16 is added drop by drop to the resulting anhydrous TBAF solution at −78° C. It is allowed to heat slowly to room temperature while being stirred and hydrolyzed with 50 ml of saturated NH₄Cl solution, if starting compound 16 can no longer be detected by thin-layer chromatography in the solution. It is extracted three times with 50 ml of Et₂O each. After drying on MgSO₄, the solvent is removed. By flash-chromatographic purification with pentane/Et₂O (20:1), 97 mg (0.465 mmol, 99%) of 4 is obtained.

The production of compounds of general formula 4a

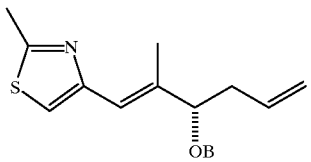

4a (B stands for benzyl, p-methoxybenzyl, tetrahydropyranyl or a silyl protective group; e.g., trialkyl or diaryl-alkyl-silyl protective groups, especially tert-butyl-dimethyl, trimethyl-silyl and diphenyl-tert-butyl-silyl groups) is carried out from by using the conventional protective group technique of etherification, see also (D. Schinzer, A. Limberg, O. M. Böhm, Chem. Eur. J. 1996, 2, 1477).

Production of 5 and compounds of general formula 9a (4'S,4R,5S,6S)-2-(2,2-Dimethyl-[1,3]dioxan-4-yl)-5-hydroxy-2,4,6-trimethyl-undec-10-en-3-one 5 and (4'S,4R,5S,6S)-2-(2,2-dimethyl-[1,3]dioxan-4-yl)-5-hydroxy-2,4,6,10-tetramethyl-undec-10-en-3-one 5a is carried out analogously to diagram 2.

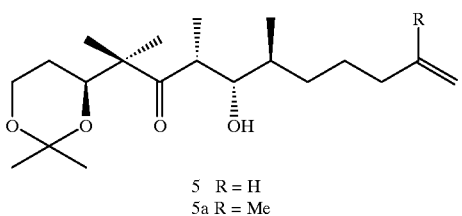

5  R = H
5a R = Me

C. H. Heathcock, C. T. Buse, W. A. Kleschick, M. C. Pirrung, J. E. Sohn, J. Lampe J. Org. Chem. 1980, 45, 1066
943 microliters (1.509 mmol, 0.98 equivalent) of a 1.6 M solution of n-BuLi in hexane is added in drops to a solution of 153 mg (1.509 mmol, 0.98 equivalent) in 1.5 ml of THF at 0° C., and it is stirred for 30 minutes, before then being cooled down to −78° C. 330 mg (1.540 mmol, 1 equivalent) of (S)-2-(2,2-dimethyl-[1,3]dioxan-4-yl)-2-methyl-pentan-3-one 2, dissolved in 1 ml of THF, is now slowly added in drops. The solution is stirred for 1 hour at −78° C. Then, 194 mg (1.540 mmol, 1 equivalent) of (S)-2-methyl-hept-6-enal 3 is added in drops, and it is stirred for 45 minutes at −78° C. The reaction solution is quenched by adding saturated NH₄Cl solution and heated to room temperature. The aqueous phase is extracted with ether, the combined organic phases are dried on MgSO₄, and the solvent is distilled off in a rotary evaporator. The residue is purified by column chromatography with pentane:diethyl ether=3:1. 369 mg (1.084 mmol, 70%) of aldol product 5 is obtained as a colorless oil.

General Data: C₂₀H₃₆O₄, MW=340.50 g/mol
Compound 5a is produced analogously. 386 mg (1.09 mmol, 64%) of 5a is obtained from 238 mg (1.70 mmol) of 3a.
(3S,6R,7S,8S)-1,3,7-Trihydroxy-4,4,6,8-tetramethyl-tridec-12-en-5-one 6 and
(3S,6R,7S,8S)-1,3,7-trihydroxy-4,4,6,8,12-pentamethyl-tridec-12-en-5-one 6a

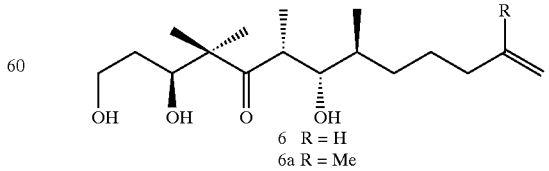

6  R = H
6a R = Me

L. A. Paquette, D. R. Sauer, D. G. Cleary, M. A. Kinsella, C. M. Blackwell, L. G. Anderson J. Am. Chem. Soc. 1992, 114, 7375–7387. A solution of 100 mg (0.294 mmol) of aldol product 5 in 14 ml of MeOH is mixed with 95 mg (0.378 mmol, 1.3 equivalents) of PPTS, stirred for 36 hours at room temperature and then quenched by adding 33 drops of saturated $NaHCO_3$ solution. The mixture is concentrated by evaporation in a rotary evaporator, and the residue is taken up in ether. It is washed with saturated NaCl solution, and the aqueous phase is extracted with ether. The combined organic phases are dried on $MgSO_4$, and the solvent is distilled off in a rotary evaporator. The residue is purified by column chromatography with diethyl ether. 78 mg (0.260 mmol, 88%) of triol 6 is obtained as a colorless oil.

General Data: $C_{17}H_{32}O_4$, MW=300.44 g/mol

Compound 6a is produced analogously. 77 mg (0.246 mmol, 91%) of 6a is obtained from 96 mg (0.270 mmol) of 5a.

(3S,6R,7S,8S)-1,3,7-Tri-(tert-butyldimethylsilyloxy)-4,4,6,8-tetramethyl-tridec-12-en-5-one 7 and (3S,6R,7S,8S)-1,3,7-tri-(tert-butyldimethylsilyloxy)-4,4,6,8,12-pentamethyl-tridec-12-en-5-one 7a

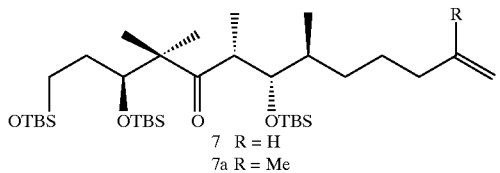

7 R = H
7a R = Me

Yuanwei Chen, Pierre Vogel, J. Org. Chem. 1994, 59, 2487–2496

963 mg (8.99 mmol, 12 equivalents) of 2,6-lutidine and 1188 mg (4.49 mmol, 6 equivalents) of tert-butyldimethylsilyl-trifluoromethanesulfonate are added in drops to a solution, cooled to −78° C., of 225 mg (0.749 mmol) of triol 6in 13 ml of $CH_2Cl_2$. It is allowed to stir for 30 minutes at −78° C. and for 3 hours at 0° C., and it is quenched with saturated $NaHCO_3$ solution. The aqueous phase is extracted with $CH_2Cl_2$. The combined organic phases are dried on $MgSO_4$, and the solvent is distilled off in a rotary evaporator. The residue is purified by column chromatography with pentane:diethyl ether=30:1. 462 mg (0.719 mmol, 96%) of trisilylated product 7is obtained as a colorless oil.

General Data: $C_{35}H_{74}O_4Si_3$, MW=643.22 g/mol

Compound 7a is produced analogously. 423 mg (0.644 mmol, 99%) of 7a is obtained from 204 mg (0.650 mmol) of 6a.

(3S,6R,7S,8S)-3,7-Di-(tert-butyldimethylsilyloxy)-1-hydroxy-4,4,6,8-tetramethyl-tridec-12-en-5one 8 and (3S,6R,7S,8S)-3,7-di-(tert-butyldimethylsilyloxy)-1-hydroxy-4,4,6,8,12-penta-methyl-tridec-12-en-5-one 8a

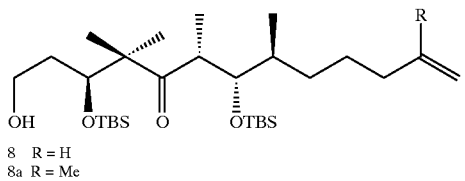

8 R = H
8a R = Me

K. C. Nicolaou, K. R. Reddy, G. Skokotas, F. Sato, X. -Y. Xiao J. Am Chem. Soc. 1992, 114, 7935. A solution of 156 mg (0.243 mmol) of trisilylated compound 7 in 6.5 ml of MeOH and 6.5 ml of $CH_2Cl_2$ is cooled to 0° C., and 11 mg of camphorsulfonic acid (0.0485 mmol, 0.2 equivalent) is added. After 5 hours of stirring at 0° C., it is quenched by the addition of saturated $NaHCO_3$ solution. The aqueous phase is extracted with $CH_2Cl_2$. The combined organic phases are dried on $MgSO_4$, and the solvent is distilled off in a rotary evaporator. The residue is purified by column chromatography with pentane:diethyl ether=3:1. 105 mg (0.199 mmol, 82%) of alcohol 8is obtained as a colorless oil.

General Data: $C_{29}H_{60}O_4Si_2$, MW=528.96 g/mol

Compound 8a is produced analogously. 101 mg (0.186 mmol, 80%) of 8a is obtained from 152 mg (0.232 mmol) of 7a.

(3S,6R,7S,8S)-3,7-Di-(tert-butyldimethylsilyloxy)-4,4,6,8-tetramethyl-5-oxo-tridec-12-enoic acid 9 and (3S,6R,7S,8S)-3,7-di-(tert-butyldimethylsilyloxy)-4,4,6,8,12-pentamethyl-5-oxo-tridec-12-enoic acid 9a

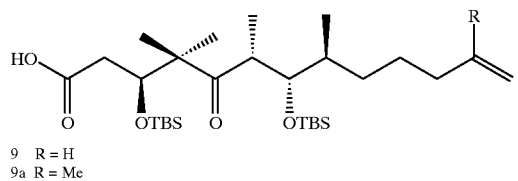

9 R = H
9a R = Me

E. J. Corey, G. Schmidt, Tetrahedron Lett. 1979, 399–402

2371 mg (6.30 mmol, 11 equivalents) of PDC, dissolved in 3 ml of DMF, is added in drops to a solution of 303 mg (0.573 mmol) of alcohol 8in 6 ml of DMF at 0° C. It is allowed to stir for 36 hours at room temperature and then poured into 50 ml of saturated NaCl solution, diluted with water and extracted with $CH_2Cl_2$. The combined organic phases are dried on $MgSO_4$, and the solvent is distilled off in a rotary evaporator. The residue is purified by column chromatography with pentane:diethyl ether=2:1. 247 mg (0.455 mmol, 79%) of acid 9 is obtained as a colorless oil.

General Data: $C_{29}H_{58}O_5Si_2$, MW=542.94 g/mol, compound 9a is produced analogously. 273 mg (0.490 mmol, 83%) of 9a is obtained from 320 mg (0.590 mmol) of 8a.

(3S,6R,7S,8S)-3,7-Di-tert-butyldimethylsilyloxy)-4,4,6,8-tetramethyl-5-oxo-tridec-12-enoic acid-(1S)-1-[(E)-1-methyl-2-(2-methyl-thiazol-4-yl)-vinyl]-but-3-enyl-ester 17 and
*(3S,6R,7S,8S)-3,7-di-tert-butyldimethylsilyloxy-4,4,6,8,12-penta-methyl-5-oxo-tridec-12-enoic acid-(1S)-1-[(E)-1-methyl-2-(2-methyl-thiazol 4-yl)-vinyl)]-but-3-enyl-ester 17 a

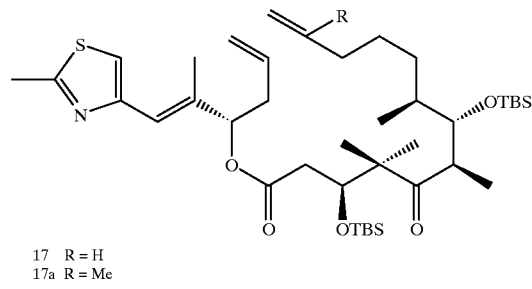

17 R = H
17a R = Me

Esterification according to B. Neises, W. Steglich Angew. Chem. [Applied Chemistry]1978, 90, 556. A solution of 145 mg (0.268 mmol) of acid 9, 56 mg (0.268 mmol) of alcohol 4 and 6.5 mg (0.0536 mmol, 0.2 equivalent) of DMAP in 1.5 ml of absolute $CH_2Cl_2$ is mixed at 0° C. with 72 mg (0.348 mmol, 1.3 equivalents) of dicyclohexylcarbodiimide. It is stirred for 10 minutes at 0° C. and for 12 hours at room temperature. After the solvent is removed and after flash-chromatography of the residue with pentane/$Et_2O$ (20:1), 157 mg (0.214 mmol, 80%) of ester 17 is obtained.

*The production of ester 17a is carried out analogously. 166 mg (0.222 mmol, 74%) of 17a is obtained from 167 mg (0.30 mmol) of 9a and the equimolar amount of 4.

(4S,7R,8S,9S,16S,13Z)4,8-Di-tert-butyldimethylsilyloxy-5,5,7,9-tetra-methyl-16-[(E)-1-methyl-2-(2-methyl-thiazol-4-yl)-vinyl]-1-oxa-cyclohexadec-13-ene-2,6-dione 18 and *(4S,7R,8S,9S,16S,13Z)4,8-di-tert-butyldimethylsilyloxy-5,5,7,9,13-pentamethyl-16-[(E)-1-methyl-2-(2-methyl-thiazol-4-yl)-vinyl]-1-oxa-cyclohexadec-13-ene-2,6-dione 18a

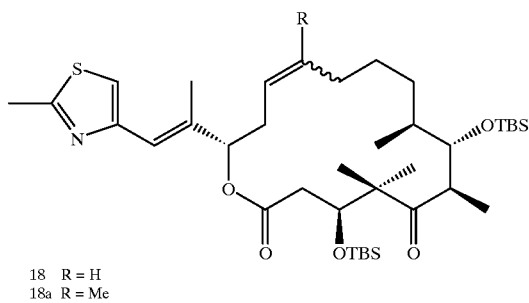

18 R = H
18a R = Me

An Ar-saturated solution of 49.3 mg (0.0671 mmol) of ester 17 in 33.5 ml of absolute $CH_2Cl_2$ (corresponding to a substrate concentration of 0.002 M) is stirred with 3.3 mg (6 mol %) of $Cl_2[RU=CHPh](PCy_3)_2$ (Cy=cyclohexyl) for 16 hours under an argon atmosphere. After the solvent is removed and after flash-chromatography of the residue with pentane/$Et_2O$ (20:1), 44 mg (0.0630 mmol, 94%) of compound 18 is obtained as a 1:1 mixture with its E-isomers. *49.0 mg (0.068 mmol, 68%) of a mixture of 18a and its E-isomers are obtained analogously from 74.8 mg (0.100 mmol) of 17a. (4S,7R,8S,9S,16S, 1Z)-4,8-Dihydroxy-5,5,7,9-tetra-methyl-16-[(E)-1-methyl-2-(2-methyl-thiazol-4-yl)-vinyl]-1-oxa-cyclohexadec-13-ene-2,6dione 19 ("Epothilone C") and *(4S,7R,8S,9S,16S, 13Z)4,8dihydroxy-5,5,7,9,13pentamethyl-16[(E)-1-methyl-2-(2-methyl-thiazol-4-yl)-vinyl]-1-oxa-cyclohexadec-13-ene-2,6dione 19a ("Epothilone D")

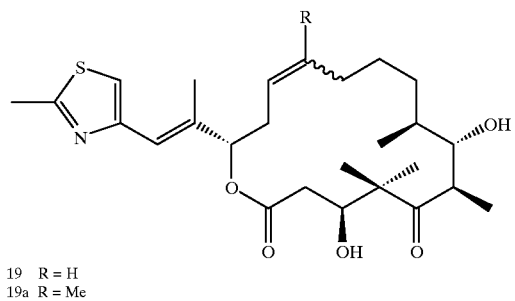

19 R = H
19a R = Me

A solution of 35.3 mg (0.05 mmol) of 18 (Z:E-mixture 1:1) in 2.4 ml of acetonitrile/$Et_2O$ (1:1) is mixed drop by drop at 0° C. with 0.27 ml of hydrofluoric acid (40%). After some glass fragments are added or after 0.027 ml of hexafluorosilicic acid (30%) is added, it is stirred for 17 hours at room temperature. The reaction mixture is mixed with 10 ml of saturated $NaHCO_3$ solution and extracted three times with 20 ml of $Et_2O$ each. The combined ether extracts are dried on $MgSO_4$. After the solvent is distilled off in a vacuum, the residue is flash-chromatographed by a silica gel column with $Et_2O$. 16.5 mg (0.0325 mmol, 65%) of 19 is obtained as a 1:1-Z:E mixture.

*20.7 mg (0.042 mmol, 70%) of 19a (as a Z:E mixture) is obtained analogously from 43.2 mg (0.06 mmol) of 18a. Epothilone A 1 and *epothilone B 1a

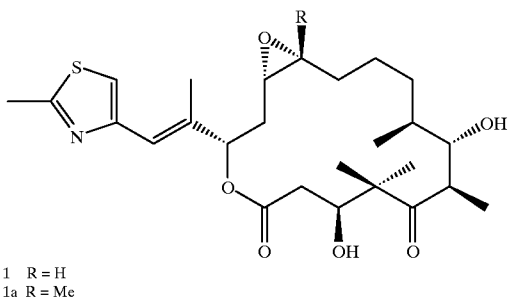

1 R = H
1a R = Me

A solution of 14.3 mg (0.03 mmol) of 19 (1:1-Z:E mixture) in 2.5 ml of $CH_2Cl_2$ is mixed at −35° C. while being stirred drop by drop with 0.36 ml (0.035 mmol, 1.2 equivalents) of a freshly produced solution of dimethyl dioxiran in acetone. It is stirred for 2 hours at −35° C., then mixed with 5 ml of a 10% aqueous solution of iron(II) sulfate and extracted three times with 10 ml of $CH_2Cl_2$ each. After the solvent is distilled off in a vacuum, the residue is flash-chromatographed by a silica gel column with $Et_2O$. 7.1 mg (0.0144 mmol, 48%) of epothilone A is obtained.

*6.2 mg (0.0123 mmol, 41%) of epothilone B is obtained analogously from 14.8 mg (0.03 mmol) of 19a.

The invention also relates to stereoisomers of the compounds according to the claims, as the latter usually accumulate within the synthesis.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula 4a

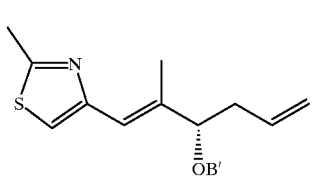

4a.

in which

B' is hydrogen, benzyl, p-methoxybenzyl, tetrahydropyranyl or a silyl protective group.

* * * * *

Disclaimer

6,043,372 — Dieter Schinzer; Anja Limberg; Oliver M. Bohm; Armin Bauer; Martin Cordes, all of Braunschweig, Germany. INTERMEDIATES IN THE PROCESS FOR PREPARING EPOTHILONES. Patent dated March 28, 2000. Disclaimer filed Aug. 21, 2002, by the assignee, Novartis AG.

The term of this patent subsequent to August 21, 2002, has been disclaimed.

*(Official Gazette May 31, 2005)*